(12) United States Patent
Harrison et al.

(10) Patent No.: US 6,997,944 B2
(45) Date of Patent: Feb. 14, 2006

(54) APPARATUS AND METHOD FOR DECREASING STENT GAP SIZE

(75) Inventors: William James Harrison, Temecula, CA (US); Andy E. Denison, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 239 days.

(21) Appl. No.: 09/928,851

(22) Filed: Aug. 13, 2001

(65) Prior Publication Data

US 2003/0033003 A1 Feb. 13, 2003

(51) Int. Cl.
*A61F 2/06* (2006.01)

(52) U.S. Cl. ..................................... 623/1.15
(58) Field of Classification Search .............. 623/1.15, 623/1.16, 1.17, 1.18
See application file for complete search history.

(56) References Cited

U.S. PATENT DOCUMENTS

| | | | |
|---|---|---|---|
| 5,514,154 A | | 5/1996 | Lau et al. |
| 5,755,771 A | * | 5/1998 | Penn et al. ................ 623/1.15 |
| 5,759,192 A | | 6/1998 | Saunders |
| 5,853,419 A | * | 12/1998 | Imran ....................... 623/1.15 |
| 5,928,280 A | * | 7/1999 | Hansen et al. ............. 623/1.15 |
| 6,171,334 B1 | | 1/2001 | Cox |
| 6,565,598 B1 | * | 5/2003 | Lootz ........................ 623/1.15 |
| 6,572,649 B2 | * | 6/2003 | Berry et al. ............... 623/1.15 |
| 2002/0010506 A1 | * | 1/2002 | Israel et al. ............... 623/1.15 |
| 2002/0165605 A1 | * | 11/2002 | Penn et al. ................ 623/1.15 |
| 2002/0188345 A1 | * | 12/2002 | Pacetti ...................... 623/1.15 |
| 2003/0014101 A1 | * | 1/2003 | Harrison .................... 623/1.15 |

FOREIGN PATENT DOCUMENTS

| | | |
|---|---|---|
| EP | 0 887 051 A1 | 12/1998 |
| EP | 1095632 A2 | 5/2001 |
| WO | WO 99/65421 A2 | 12/1999 |

* cited by examiner

*Primary Examiner*—Michael Thaler
(74) *Attorney, Agent, or Firm*—Fulwider Patton LLP

(57) ABSTRACT

An expandable intraluminal stent having a strut pattern made from a plurality of triangular cells is disclosed. Each triangular cell is formed from at least two V struts of different magnitudes aligned in phase and joined at opposite ends forming two opposed vertices of the triangle. A series of triangular cells are joined at the vertices to form a ring. The series of triangular cells may be arranged to form peaks in the ring, peaks and valleys in the ring, or a combination thereof. A plurality of the rings are aligned coaxially and joined by connecting elements to form a tubular shape. Use of the double V strut formation in the rings increases vessel wall coverage, reduces gap sizes, and does not impair the compressability of the stent for a small profile for delivery.

16 Claims, 6 Drawing Sheets

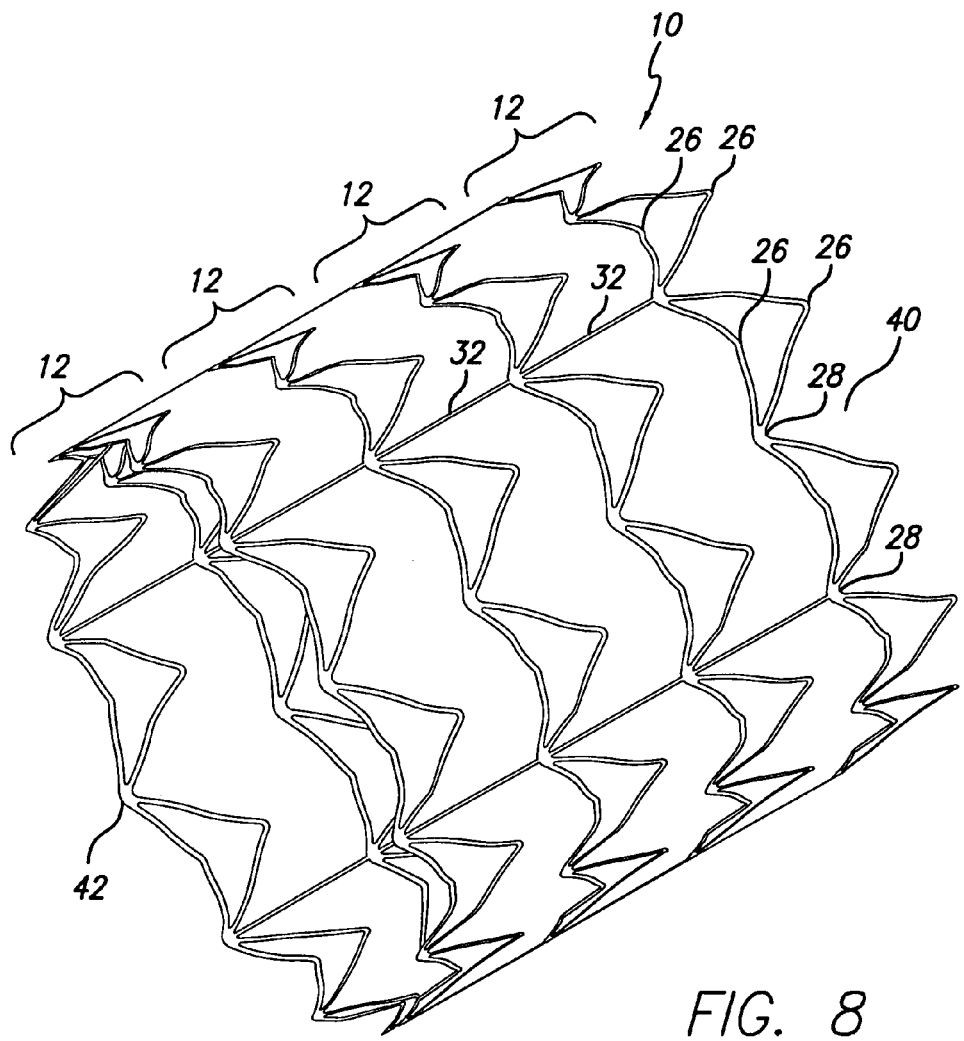
FIG. 8
FIG. 9
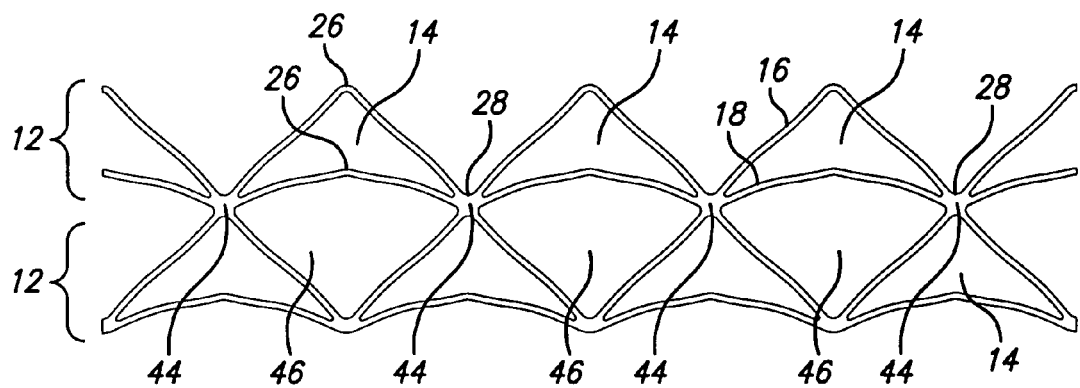

APPARATUS AND METHOD FOR DECREASING STENT GAP SIZE

BACKGROUND OF THE INVENTION

The present invention relates to expandable endoprosthetic devices, generally called stents, which are implanted in a patient's body lumen, such as blood vessel, to maintain the patency thereof. More particularly, the present invention relates to a triangular shape strut pattern for increased coverage and reduced gap size between the struts.

Stents are generally tubular-shaped devices which function to hold open a segment of a diseased blood vessel or other anatomical lumen. For example, stents are useful in the treatment and repair of blood vessels after a stenosis has been compressed by a procedure such as percutaneous transluminal coronary angioplasty (PTCA), percutaneous transluminal angioplasty (PTA), or when the stenosis is removed by atherectomy or other means. They are also suitable for use to support and scaffold a dissected arterial lining that might occlude the fluid passageway or to repair an injured vessel wall as in an aneurysm.

Various means are known in the art to deliver and implant stents. One method frequently described for delivering a stent to a desired intraluminal location involves mounting an expandable stent on an expandable member such as a balloon provided on the distal end of an intravascular catheter, advancing the catheter to the desired location within a patient's body lumen, inflating the balloon on the catheter to expand the stent into a permanently expanded condition, deflating the balloon, and withdrawing the catheter.

As stents are normally employed to hold open an otherwise constricted or occluded lumen, a stent must exhibit sufficient radial or hoop strength in its expanded state to effectively counter the anticipated closing forces. Not only is it advantageous to distribute such loads over as much of the stent as possible, but it is most beneficial to distribute the load over as much of the lumen wall as possible. This helps minimize injury to the vessel wall. Also by minimizing the gaps between stent struts, it is possible to prevent prolapse of the plaque or the vessel wall in the open areas between the struts into the lumen. As a consequence, it is desirable to maximize the coverage of the lumen wall by creating small, uniform openings between the stent struts. It is, however, simultaneously necessary for the stent to be as small and compact as possible in its collapsed state in order to facilitate its advancement through the lumen to the delivery site. As large an expansion ratio as possible is therefore most desirable.

A number of very different approaches have been devised in an effort to address these various requirements. One approach calls for the stent to be constructed entirely of wire. The wire is bent, woven, or coiled to define a generally cylindrical structure in a configuration that has the ability to undergo radial expansion. The use of wire, however, has a number of disadvantages. For example, a substantially constant cross-sectional area of a wire might cause greater or lesser than an ideal amount of material to be concentrated at certain locations along the stent. Additionally, wire has limitations with respect to the shapes it can be formed into thus impairing the expansion ratio, coverage area, and strength that can ultimately be attained. Regarding strength, some have welded sections of wire together to increase strength albeit with a substantial increase in manufacturing costs and possible materials problems caused by welding heat.

As an alternative to wire-based structures, stents have been constructed from tube stock. By selectively removing material from such tubular starting material, a desired degree of flexibility and expandability can be imparted to the structure. Chemical etching techniques as well as laser-cutting processes are utilized to remove material from the tube. Laser cutting provides for a high degree of precision and accuracy through which very intricate shapes of material can be removed leaving behind a complex strut pattern.

The performance parameters of a stent is often a function of the pattern in which material is removed from the tube stock. The selection of a particular pattern sometimes has a profound effect on the coverage area, expansion ratio, and strength of the resulting stent.

As shown in FIGS. 1–3, prior art stent designs have attempted to increase vessel coverage while maintaining expansion ratio and strength. For instance, the stent design as shown in FIG. 1 illustrates a stent 1 having bridging elements 2. Here, the bridging element 2 is widened to increase the surface area 3 in order to achieve a commensurate increase in vessel coverage. Yet another prior art stent 40, as shown in FIG. 2, has a strut pattern shown in the compressed state that increases vessel coverage by increasing the density of the struts 5 forming the stent body. The effectiveness of this strut pattern lies in the ability to "nest" the strut pattern. That is, the peaks 7 of one ring fit into the interstices of an adjacent ring and the valleys 8 of the adjacent ring fit into the interstices of the first ring so that two adjacent rings essentially overlap. The struts 5 are also curved to pack closely to the bridge member 6.

In FIG. 3, the prior art strut pattern is identical to that shown in FIG. 2, but is depicted in the fully expanded state. The nested struts have moved away from each other without structures interfering in that motion. The prior art stent designs thus provide improved vessel coverage without dramatically increasing the quantity of material used. However, there is room for further improvements.

Additionally, one of the continuing goals of endovascular therapy includes providing stenting solutions to smaller and smaller vessels more distant along the patient's vasculature away from the physician. To this end, prior art stents have been designed and developed to exhibit higher degrees of compressibility to achieve a smaller compressed delivery profile capable of fulfilling the goal of delivery to distant vessels. One approach to stent design capable of achieving a smaller compressed stent profile is through reducing the mass to space ratio of the stent body. Having less mass and high expandability, the stent may be compressed into a highly compact profile capable of achieving the goal of delivery to smaller and more distant vessels.

Yet a continuing obstacle encountered with prior art designs attempting to reduce the mass to space ratio is that as the mass to space ratio of the stent decreases, so does the vessel coverage provided by the same stent. As can be seen from the foregoing discussion, the goal of decreasing the compressed profile of the stent by reducing the amount of structural material is somewhat antithetical to the goal of providing increased vessel coverage by using more stent material to increase the stent surface area.

Therefore, what has been needed and heretofore unavailable is a highly compressible stent for delivery into highly tortuous and distant vessels, yet still is able to provide acceptable coverage of the target vessel in order to decrease the possibility of vessel wall or plaque prolapse. The present invention satisfies these needs.

SUMMARY OF THE INVENTION

The present invention is directed to an expandable intraluminal stent, made from a plurality of rings aligned along a common axis to form a tubular shape; wherein each ring includes a plurality of triangular cells; wherein each triangular cell is formed from at least two V struts having different amplitudes with respective large angle vertices that are aligned in phase and with opposite ends joined to form small angle vertices; wherein the triangular cells are joined together to form the ring at the small angle vertices. The stent includes at least one connecting element joining the plurality of rings to each other.

In a preferred embodiment, the stent includes a plurality of parallel longitudinal connecting elements extending through the joined small angle vertices. Alternatively, one ring may be joined to an adjacent ring by joining the vertices of the triangular cells; in this embodiment, the connecting element has minimal longitudinal dimension. The vertices of the triangular cells preferably have radii of curvatures to lower stress concentrations. In various alternative embodiments, the triangular cells in one ring can be in-phase or out of phase (staggered) relative to the triangular cells in an adjacent ring, and the longitudinal connecting elements may be aligned end-to-end in a row or staggered relative to each other. Each of the arm segments forming the V strut may be straight or curved, and the series of triangular cells forming a single ring may have smooth transitions to provide an overall serpentine or wave-like appearance.

The present invention stent may be made of a super elastic metallic alloy such as nitinol. Under this construction, the stent is self-expanding and exhibits high resilience. Alternatively, the present invention stent may be balloon-expandable, in which case a plastically-deformable material such as stainless steel or the like can be used.

Accordingly, the present invention stent is relatively flexible along its longitudinal axis to facilitate delivery through tortuous body lumens, but is stiff and stable enough radially in an expanded condition to maintain the patency of a body lumen when implanted therein. Furthermore, the present invention stent by virtue of its double V strut pattern gives increased vessel coverage with reduced gap size thus decreasing the amount and likelihood of vessel wall or plaque prolapse without compromise to compressibility of the stent.

BRIEF DESCRIPTION OF THE DRAWINGS

FIG. 8 is perspective view of a section of the preferred embodiment stent.

FIG. 9 is a flattened plan view of a section of a strut pattern of an alternative embodiment stent in its expanded state showing staggered triangular cells and connecting elements that have minimal length.

DETAILED DESCRIPTION OF THE PREFERRED EMBODIMENTS

The present invention in a preferred embodiment is directed to an expandable stent that can be implanted in the body lumen. In a preferred embodiment, the stent has a plurality of rings aligned along a common longitudinal axis to form a tubular shape, wherein each ring includes a plurality of triangular cells and each cell includes at least two V struts having different amplitudes. The V struts are aligned in phase and joined at the opposite ends of the V struts to form the triangular shape cell. The stent further has one or more connecting elements joining the plurality of rings. Such a construction according to the present invention increases coverage by the stent, decreases the gap size between the struts, while allowing the stent to be compressed into a small profile for ease of deliverability.

Figure 1:
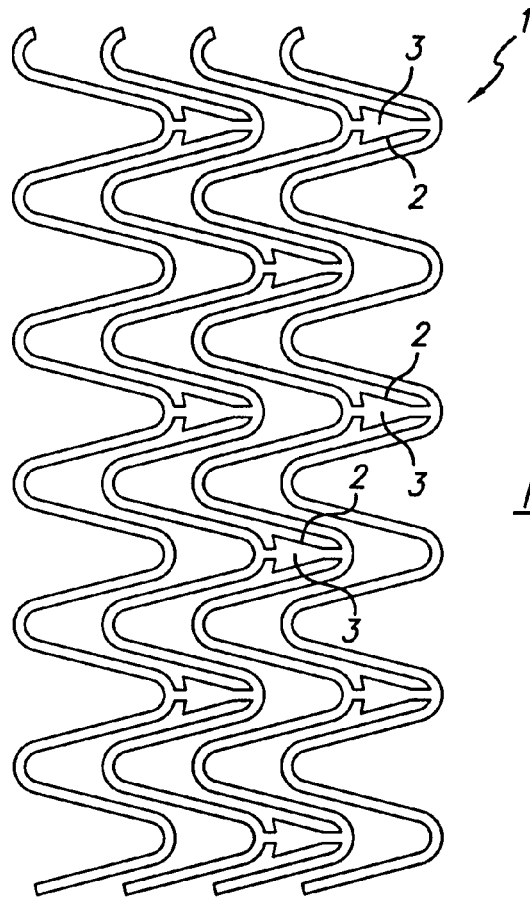
FIG. 1 is flattened plan view of a section of a prior art stent strut pattern having widened bridging members that provide increased coverage.
Figure 2:
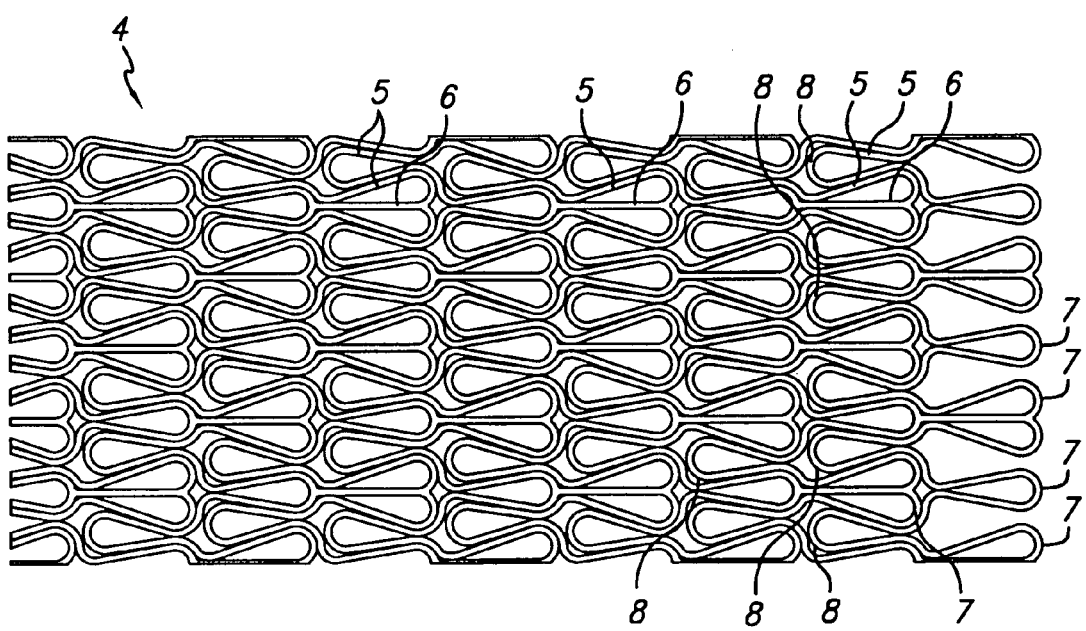
FIG. 2 is a flattened plan view of a section of another prior art stent strut pattern, in the compressed state, depicting denser packing for enhanced coverage area.
Figure 3:
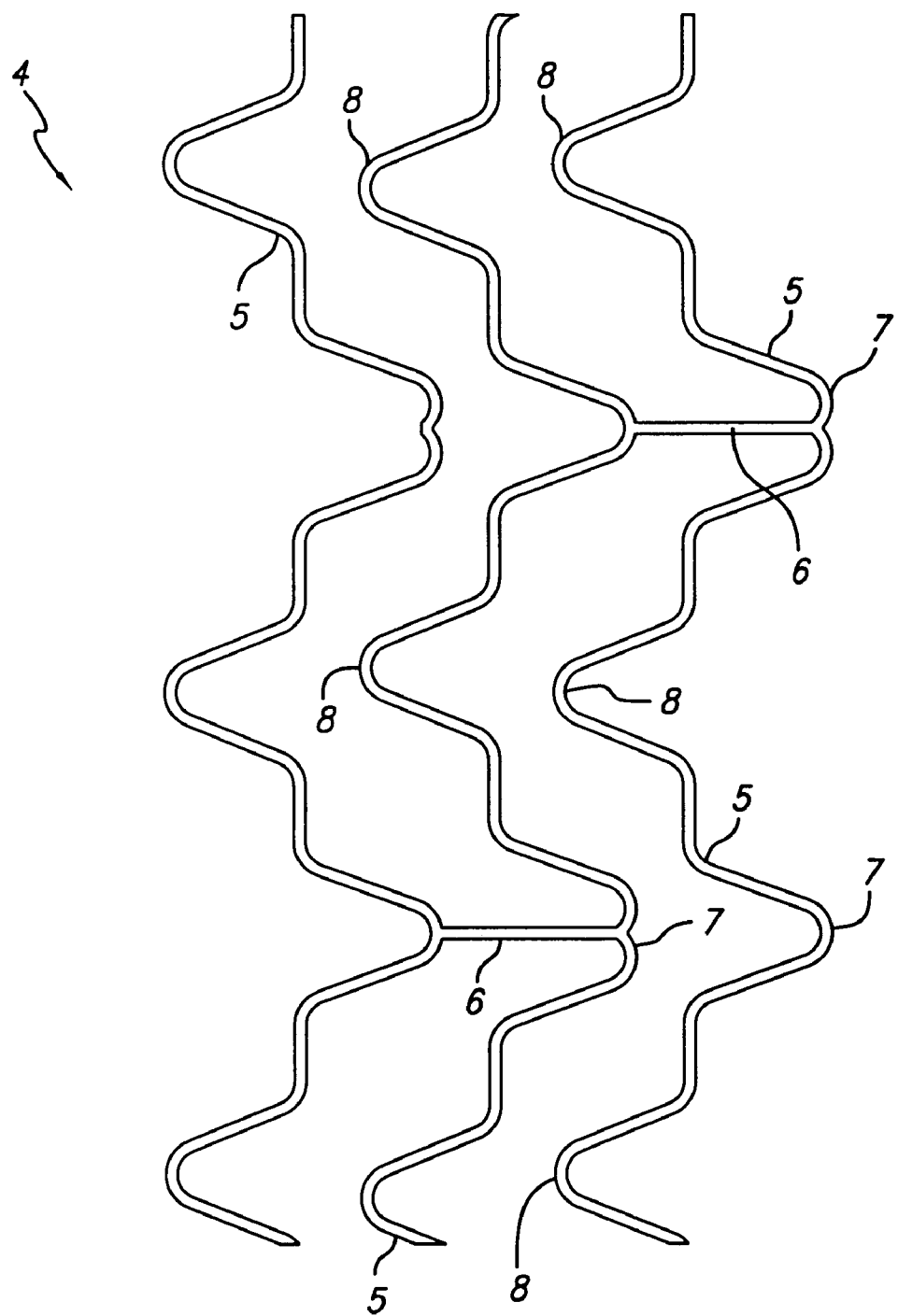
FIG. 3 is a flattened plan view of the prior art stent strut pattern of FIG. 2 in a fully expanded state.
Figure 4:
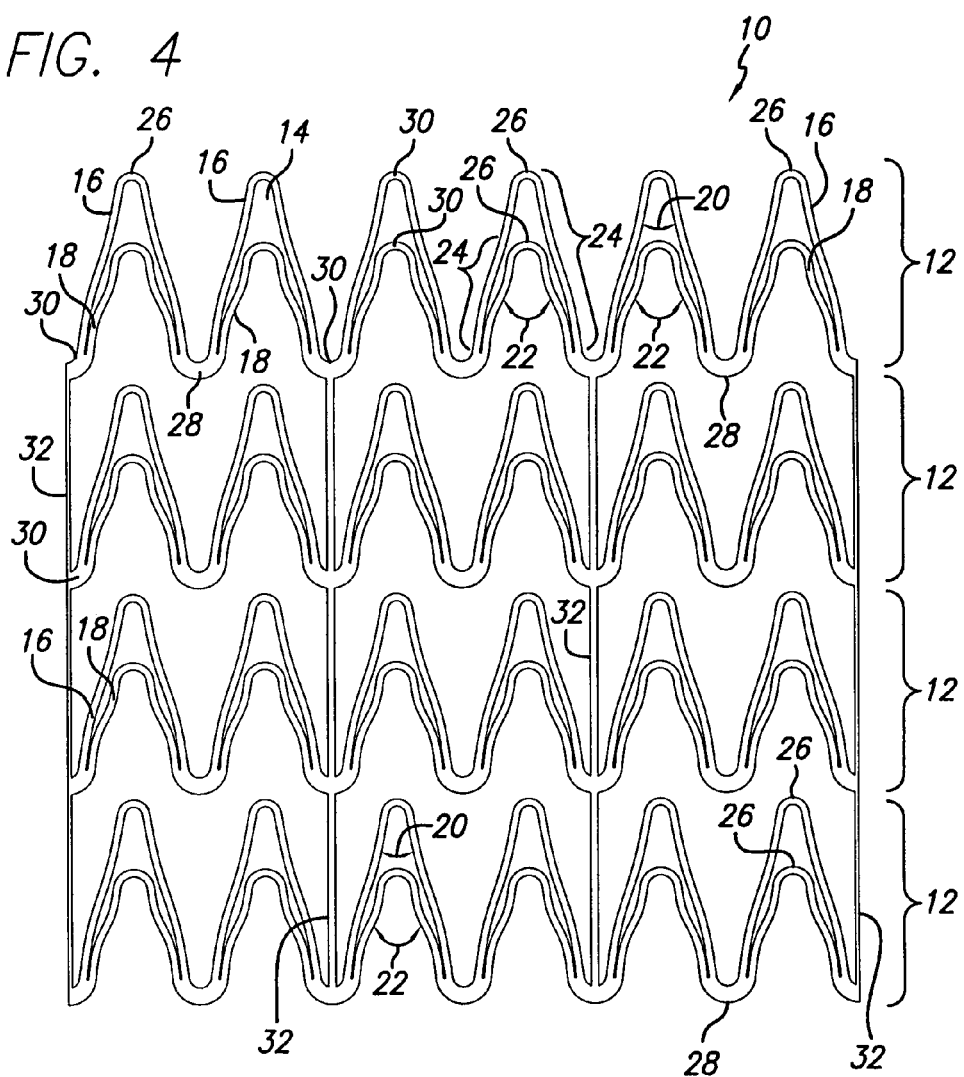
FIG. 4 is a flattened plan view of a section of a preferred embodiment stent of the present invention in a compressed state showing double V struts forming a pattern of triangular cells.

FIG. 4 is a flattened plan view of a segment of the strut pattern for the present invention stent 10 in the compressed state. The stent 10 preferably has a plurality of rings 12 arranged along a common longitudinal axis to form a tubular shape. Each ring as seen in FIG. 4 is formed from a plurality of triangular cells 14.

The triangular cell 14 is constructed preferably by joining two V struts 16, 18 of different amplitudes; that is, the peak 26 of one V strut 16 is greater than the peak 26 of the other V strut 18. Of course, there can be more than the two (i.e., three, four, etc.) V struts per triangular cell for even greater wall coverage. Based strictly on the orientation of the V struts 16, 18 in FIG. 4, they may also be described as inverted, V-shape struts. No matter upright or inverted, each V strut 16, 18 has an included angle 20, 22 corresponding to each peak 26. Accordingly, the triangular cell 14 has a large angle vertex coinciding with included angle 20 and two opposed small angle vertices coinciding with where the opposite ends of the V struts 16, 18 are joined.

The included angles 20, 22 may have the same or different magnitudes in order to allow connection at the base, and are bounded by the arm segments 24 forming the sides of the V. These arm segments 24 may be curved, straight, or a combination of the two. The preferred embodiment arm segments 24 have a shoulder or outward bulge that improves optional nesting of the peaks 26 and minimizes possible out-of-plane twisting by the struts during expansion.

Another way to look at an individual ring 12 in FIG. 4 is to discern a serpentine waveform created by connecting the double V struts 16, 18 end-to-end. The serpentine waveform has a continuous, repeating pattern of peaks 26 and valleys 28. This exemplary serpentine pattern in is different from conventional strut patterns, because of the presence of the double struts at the peaks 26 that are then joined into single struts at the valleys 28. The double struts are created by having different amplitude peaks 26 while having the same amplitude valleys 28.

In the preferred embodiment, the peaks 26 and valleys 28 have various radii of curvatures 30 or fillets to minimize stress concentrations in these areas. It is also possible to increase the width, thickness, mass, or a combination thereof in these areas to decrease stress concentrations. In the preferred embodiment, to minimize stress concentrations, the valleys 28 have optionally included extra mass, surface area, or the like. This area of extra mass or surface area coincides with the confluence of the ends of the V struts 16, 18 at the valleys 28 of the serpentine waveform. Depending on manufacturing methods used to create the stent 10 the valley 28 can be a weld joint or simply an area of greater mass or surface area left over after laser cutting or chemical etching.

A series of the triangular cells 14 are joined together at the valleys 28 to create a continuous ring 12 or annulus. Each ring 12 is then joined to an adjacent ring 12 by use of a connecting element 32. The connecting element 32 may have a longitudinal dimension or length parallel to the longitudinal axis of the stent 10 as shown in FIG. 4, or it may have minimal longitudinal dimension as shown in the alternative embodiment in FIG. 9. The connecting element in alternative embodiments may be sloped with a length not parallel to the longitudinal axis of the stent, or it may have bends or curves to change the flexibility of the stent.

Figure 7:
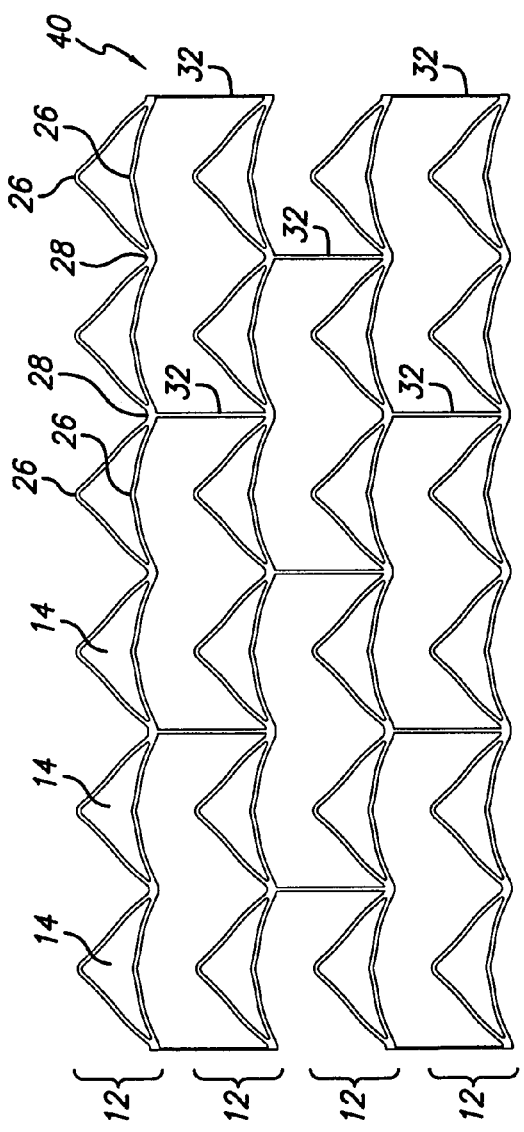
FIG. 7 is a flattened plan view of a section of an alternative embodiment stent in its fully expanded state having staggered connecting elements.

Furthermore, in the exemplary embodiment shown in FIG. 4, the connecting elements 32 are aligned end-to-end in a row parallel to the longitudinal axis of the stent 10. The connecting elements 32 further pass through the valleys 28 of each ring 12. There are preferably two triangular cells 14 between each connecting element 32. Of course, the connecting elements 32 may be arranged in a variety of patterns in which there may be more or fewer than two triangular cells 14 separating adjacent connecting elements 32. Alternatively, the connecting elements may be staggered from one row to the next as shown in FIG. 7.

Figure 5:
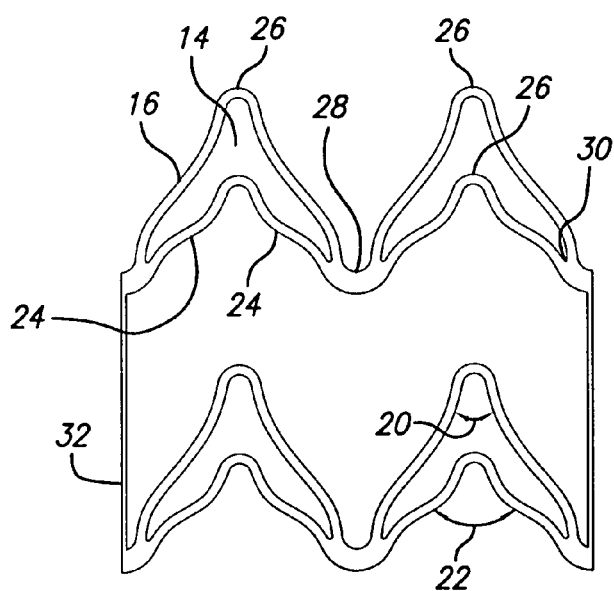
FIG. 5 is a plan view of a portion of the strut pattern of FIG. 4 in which the stent is in a partially expanded state.

FIG. 5 is a flattened plan view of a portion of the strut pattern shown in FIG. 4 in which the stent 10 has been partially expanded. As such, the included angles 20, 22 have increased as compared to their magnitudes in FIG. 4. Also notable is that as the stent 10 begins to expand radially, although the distance from one ring 12 to the adjacent ring 12 is fixed by the length of the connecting element 32 joining the two, the peak-to-peak 26 distance between adjacent rings 12 increases since the amplitudes of the peaks 26 decrease during this expansion. This is apparent from comparing the relative amplitudes of the peaks 26 in FIG. 5 versus FIG. 4.

In various alternative embodiments, the length of the connecting element 32 may be increased or, more specifically, decreased to more closely "nest" the serpentine strut pattern of one ring 12 into its neighboring ring 12. In such a construction, the amplitudes of the peaks 26 in one ring 12 would overlap the amplitudes of the valleys 28 in an adjacent ring. Shortening the connecting elements 32 decreases flexibility and gap sizes, but increases vessel wall coverage.

Figure 6:
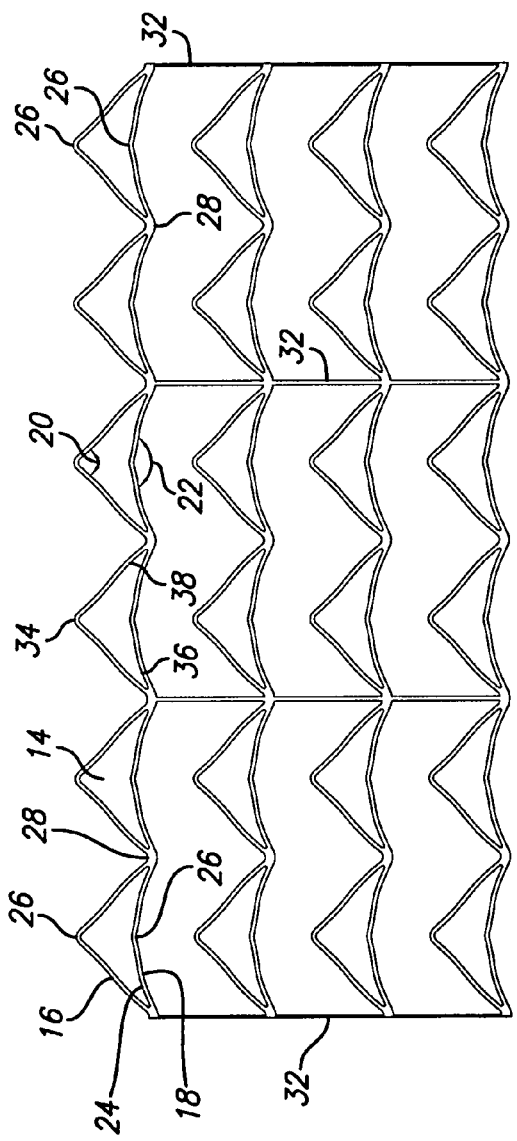
FIG. 6 is a flattened plan view of the strut pattern of FIG. 4 in a fully expanded state.

FIG. 6 is a flattened plan view of the segment of the stent 10 shown in FIG. 4 in the fully expanded state. As more readily seen in this view, the triangular cell 14 has a distinct triangular shape with three vertices: a large angle vertex 34, and two opposed small angle vertices 36, 38. In the preferred embodiment, the triangular cell 14 is preferably an isosceles type triangle, but other triangles such as a scalene or an equilateral triangle are also contemplated. Each type of triangle has its merit depending on the medical application in the body.

In the fully expanded state shown in FIG. 6, the included angles 20, 22 have expanded even farther out thereby decreasing the amplitudes of the peaks 26. Under these conditions, it is apparent that the present invention stent 10 provides the added benefit of having double V struts 16, 18 that significantly improve support for the vessel wall. The increased coverage reduces the likelihood of prolapse of plaque or the wall lining. By the same token, the double V struts 16, 18 do not inhibit compressibility of the stent to enable a small delivery profile.

FIG. 7 is a flattened plan view of a segment of an alternative embodiment stent in which the connecting elements 32 are staggered along the length of the stent 40. In other words, the strut pattern shown in FIG. 7 alternates the location of the connecting element 32 from one ring 12 to the next, although it is further contemplated that other patterns such as having two or three connecting elements aligned in a row for two or three rings can also be used. The strut pattern may further stagger the connecting elements 32 by changing the location of the connecting element 32 in one ring 12 relative to the next ring 12 by sequentially shifting the location of the connecting element by a uniform magnitude of angular degrees such as 30, 45, 60, 90, 120, etc. Further, the number of connecting elements 32 can be reduced down to one between adjacent rings 12 or can be increased to as many as needed to increase the longitudinal rigidity of the stent 40. Although not shown, a connecting element may join adjacent rings by connecting the valley of one ring to the peak of an adjacent ring.

FIG. 8 provides a perspective view of a section of the preferred embodiment stent 10 shown in FIG. 4. The stent 10 is shown in the expanded state and has a tubular form. The stent has preferably a distal end 40 and a proximal end 42. Obviously for the sake of illustration, the length of the stent has been shortened. The number and arrangement of rings 12 used, the number and location of cells 14 used in each ring, the number and location of connecting elements used 32, can all be varied individually or in combination from that shown. Moreover, it is also contemplated that the stent 10 can be inverted in use so that the distal end 40 becomes the proximal end and the proximal end 42 becomes the distal end in certain applications where, for example, the distal end requires greater rigidity or strength.

FIG. 9 is a flattened plan view of a portion of an alternative embodiment strut pattern of the present invention. In this view, the stent is in the fully expanded state. Triangular cells 14 are still present as are the peaks and valleys 26, 28, but the location of the triangular cells 14 are staggered from one ring 12 to the next. Also, what is different from the previous embodiments is that the longitudinal dimension of the connecting element 32 has been minimized to create a short connecting element 44.

The short connecting element 44 coincides with the valleys and peaks of the joined triangular cells 14 of adjacent rings 12. The triangular cells 14 are constructed as before by the double V struts 16, 18, with the joined ends also coinciding with the short connecting element 44. The short connecting elements 44 or joints are areas of material left over by laser cutting, machining, or etching; or they could be beads formed when the struts are welded, soldered, or bonded. In the exemplary embodiment shown in FIG. 9, the short connecting element 44 or joint has an increased surface area or mass to decrease stress concentrations and to increase the strength of that area. To be sure, alternative embodiments of the short connecting element may have a shape, thickness, width, length, surface area, mass, different from that shown. An inverted triangular cell 46 is formed as a by product of this strut pattern.

Figure 10:
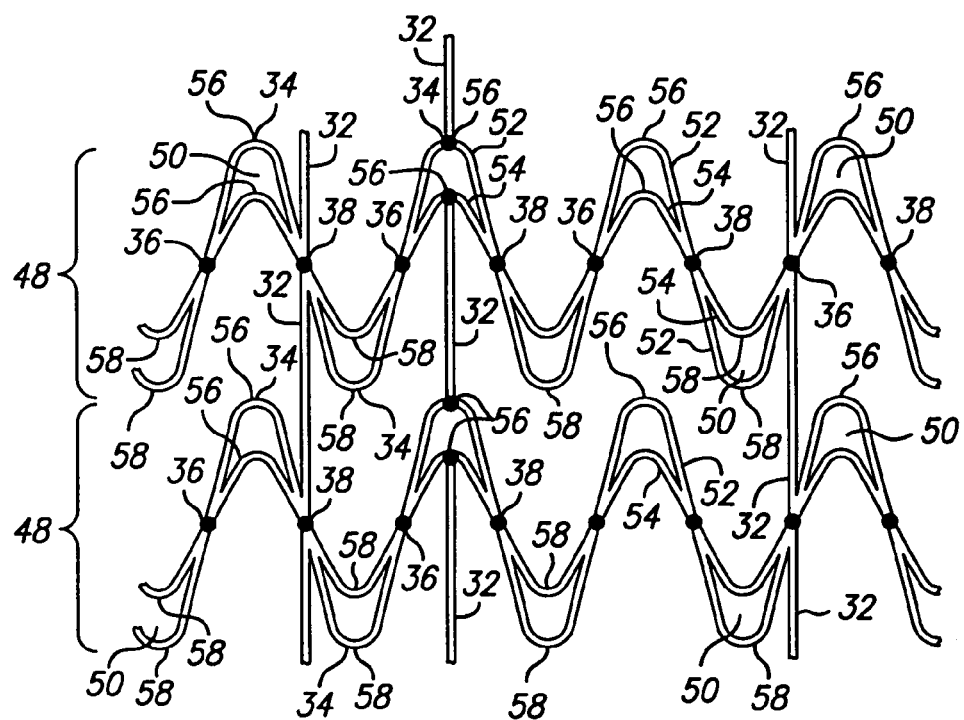
FIG. 10 is a flattened plan view of a section of a strut pattern of another alternative embodiment stent in its compressed state showing a series of triangular cells forming the peaks and valleys of the rings.

FIG. 10 is a plan view of a flattened section of an alternative embodiment strut pattern for a stent shown when the stent is in the compressed state. The strut pattern includes a plurality of triangular cells 50 arranged in a series forming peaks 56 and valleys 58 in each ring 48. Each triangular cell 50 has a large angle vertex 34 and two opposed small angle vertices 36, 38. The peaks 56 and valleys 58 may include optional radii as shown to reduce stress concentrations at high flexure or other stress points. The end result is a serpentine wave pattern forming each ring 48.

Each triangular cell 50 is preferably constructed from a double V strut 52, 54 configuration in which the V's have different amplitudes and are arranged in phase as illustrated in FIG. 10. The double V strut 52, 54 configuration is also used to form the valleys 58. In fact, the valleys 58 in this exemplary embodiment are the mirror image of the peaks 56. More than two V struts 52, 54 may be used to create each peak 56 or valley 58. In the illustrated embodiment, the double V struts 52, 54 do not have the optional shoulders or other curves shown in the FIG. 4 embodiment. The opposite ends of the double V struts 52, 54 are joined at the small angle vertices 36, 38 to form each triangular cell 50. The triangular shape is slightly distorted in the compressed state shown in FIG. 10, but is more readily apparent in the expanded state shown in FIG. 11.

Each ring 48 is connected to an adjacent ring 48 by use of a preferably straight connecting element 32. Each connecting element 32 has a longitudinal dimension or length that stretches parallel to the longitudinal axis of the stent. The connecting elements 32 may pass through the small angle vertices 36, 38, or in the alternative, join pairs of adjacent rings 48 peak-to-peak 56, both illustrated in FIG. 10. In another alternative embodiment (not shown), the connecting elements 32 may join adjacent rings 48 valley-to-valley 58.

The small angle vertices 36, 38 may possess increased mass to increase the strength of the material at high stress points. The intersection of a connecting element 32 with a peak 56 or a valley 58 may also be reinforced with increased mass. The increased mass may be achieved by increased surface area, thickness, width, length, material density as by using a weld or adhesive bead, etc. To further reduce stress concentrations, as with the peaks 56 and valleys 58, the small angle vertices 36, 38 may include a curve, radius, or fillet especially at an intersection with a connecting element 32 to minimize sharp corners or transitions.

The thickness or width of each strut may be increased or the strut shortened in any combination to improve vessel scaffolding, hoop strength, and wall coverage. The thickness or width of the struts may be reduced or the strut lengths increased in any combination to improve flexibility, ease of crimping on a catheter, and deliverability of the stent. In various alternative embodiments (not shown), the lengths of the connecting elements 32 in FIG. 10 may be shortened so that the rings 48 are closer to each other than that shown, or even closer yet in a nested formation. In the nested formation, the peaks 56 of one ring 48 extend into the interstitial space between the valleys 58 of an adjacent ring 48.

Figure 11:
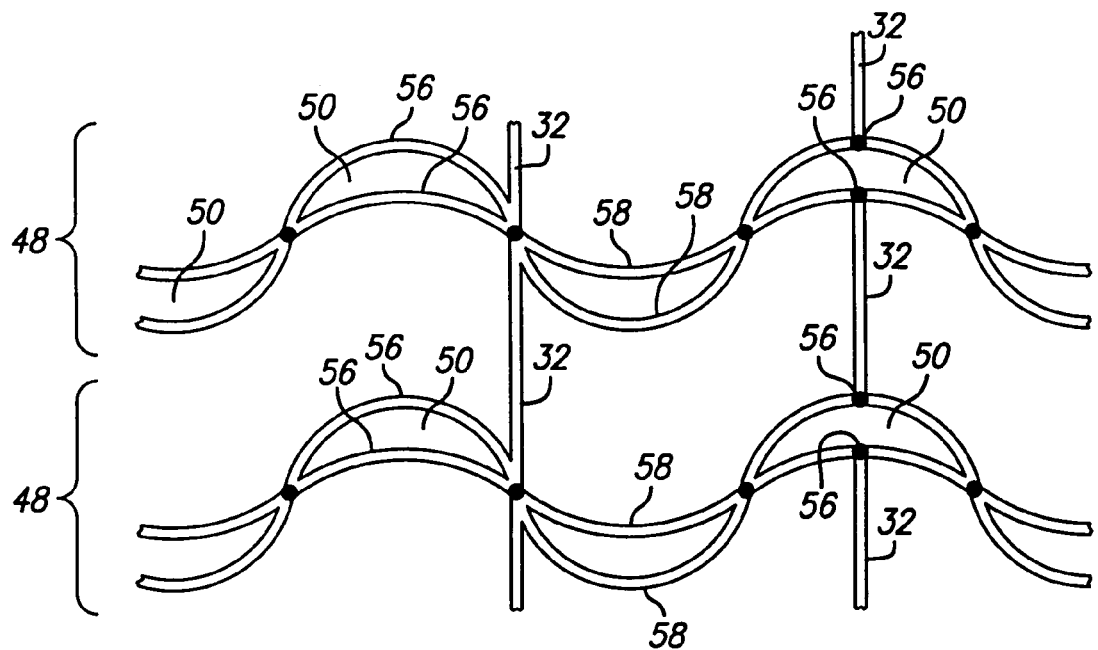
FIG. 11 is a flattened plan view of the strut pattern from FIG. 10 in the expanded state.

FIG. 11 is a plan view of the strut pattern of FIG. 10 shown in the expanded state. Although the distance between the rings 48 is set by the lengths of the connecting elements 32 which preferably remains fixed, the amplitudes of the peaks 56 and valleys 58 have decreased as compared to their magnitudes in the compressed state illustrated in FIG. 10. The distances between rings 48 may of course change, for example, in a self-expanding nitinol stent in which the longitudinal component—the connecting element—has a curve or curves that expand longitudinally with the radial expansion of the stent.

The mechanical properties of the present invention stent may be varied by alteration of the serpentine strut pattern forming the rings. The amplitudes of the peaks and valleys of the serpentine waveform, how many peaks and valleys per unit of circumferential distance along the ring, the thickness, width, or area of portions of the waveform, are chosen to fill particular engineering requirements for the stent. Such requirements include hoop strength, bending flexibility, expansion behavior, compressibility, gap size, etc. The number of peaks and valleys may also be varied to accommodate specific placement of the connecting elements. The connecting elements may be positioned at the peaks as in FIGS. 10–11 or at the valleys as seen in FIGS. 4–9.

In the preferred embodiment shown in FIG. 4, the serpentine waveform may have four to sixteen peaks 26 and valleys 28 of each per ring 12. The strut width of the longer arm segment 24 ranges from 0.002 to 0.020 inch; the strut width of the shorter arm segment 24 ranges from 0.001 to 0.020 inch. The strut length (measured peak to valley) of the longer arm segment 24 ranges from 0.02 to 0.5 inch; the strut length of the shorter arm segment 24 ranges from 0.01 to 0.4 inch. The struts may range in thickness from 0.002 to 0.020 inch.

The stent of the present invention can be made in many ways. One method of making the stent is to coat a length of thin-walled, tube stock made from stainless steel or the like with a material that resists chemical etchants. Next, portions of the coating are removed to expose the underlying tubing which is to be removed. Subsequent etching removes the exposed portions of the metallic tubing, but leaves relatively untouched the coated portions of the metallic tubing that are to form the stent.

Alternatively, the strut pattern maybe cut out of the tube stock by laser. Such a process is shown in, for example, U.S. Pat. No. 5,759,192 issued to R. Saunders, entitled "Method and Apparatus for Direct Laser Cutting of Metal Stents," whose entire contents are hereby incorporated by reference. Other machining methods for creating strut patterns may be employed, such as grinding, punching, electrical discharge machining (EDM), etc.

The tube stock may be made of suitable biocompatible material such as stainless steel, titanium, tantalum, super elastic NiTi alloys, and even high strength thermoplastic polymers. The stent diameter is very small, so the tubing from which it is made must necessarily also have a small diameter. Typically the exemplary embodiment stent has an outer diameter on the order of about 0.1 inch in the unexpanded condition, the same outer diameter of the tubing from which it is made, and can be expanded to an outer diameter of 1.0 inch or more. The wall thickness of the tubing is about 0.020 inch. In the instance when the stent is plastic, it would have to be heated within the arterial site where the stent is expanded to facilitate the expansion of the stent. Once expanded, it is cooled to retain its expanded state. The stent may be conveniently heated by heating the fluid within the balloon by a suitable system.

As mentioned above, the present invention stent may also be made from super elastic materials such as binary or ternary NiTi alloys known in the art. The super elastic properties of a nitinol stent allow the device to self-expand at the delivery site without the need of an inflation balloon although one may also be used. The high resilience of a nitinol stent allows it to resist impact forces and thus enjoys crush resistance. In this embodiment, the stent could be manufactured at its preferred final size maximum of approximately 1 inch diameter.

While the present invention has been illustrated and described herein in terms of its use as an intravascular stent, it will be apparent to those skilled in the art that the present invention can be used in many other applications, such as to expand prostatic urethras in cases of prostate hyperplasia. Other modifications and improvements may be made without departing from the scope of the present invention.

What is claimed is:

1. An expandable intraluminal stent, comprising:
a plurality of rings aligned along a common axis to form a tubular shape;
wherein each ring includes a plurality of cells, each cell being defined by at least two V struts of different amplitudes that are aligned in phase and nested within one another, wherein each of said V struts is defined by two arm segments converging at one end to define a first vertex that is otherwise unattached to any other stent structure and diverging at the opposite end such that each defines a second vertex with an arm segment of a V strut with which it is nested, and wherein each second vertex is attached to a second vertex of an adjacent cell by a link; and
a connecting element extending between a link between adjacent cells in one ring with a link between adjacent cells of an adjacent ring.

2. The expandable intraluminal stent of claim 1, wherein the arm segments are curved.

3. The expandable intraluminal stent of claim 1, wherein the connecting element is oriented generally parallel to the common axis.

4. The expandable intraluminal stent of claim 1, wherein the stent includes a plurality of connecting elements aligned in phase between rings.

5. The expandable intraluminal stent of claim 1, wherein the stent includes a plurality of connecting elements aligned out of phase between rings.

6. The expandable intraluminal stent of claim 1, wherein at least one of the second vertices includes increased mass.

7. The expandable intraluminal stent of claim 1, wherein at least one of the first vertices includes increased mass.

8. The expandable intraluminal stent of claim 1, wherein the links are curved.

9. The expandable intraluminal stent of claim 1, wherein the cells are triangular upon stent expansion.

10. An expandable intraluminal stent, comprising:
a plurality of rings aligned along a common axis to form a tubular shape;
wherein each ring includes a plurality of cells;
wherein each cell is formed from at least two nested V struts of differing amplitudes converging from common points to define peaks, wherein said common points of adjacent cells are linked by valleys, and wherein said peaks of each cell are free to shift relative to one another during expansion of said stent; and
a connecting element extending between valleys of adjacent rings.

11. The expandable intraluminal stent of claim 10, wherein the stent includes a superelastic metallic alloy and is self-expanding.

12. The expandable intraluminal stent of claim 10, wherein the stent includes a low elasticity metal and the stent is balloon expandable.

13. The expandable intraluminal stent of claim 10, wherein said valleys are curved.

14. The expandable intraluminal stent of claim 10, wherein a plurality of connecting elements extend between valleys of adjacent rings and adjacent connecting elements are separated by at least two cells.

15. The expandable intraluminal stent of claim 10, wherein the V struts have curved segments.

16. The expandable intraluminal stent of claim 10, wherein the cells are triangular upon stent expansion.

* * * * *